(12) United States Patent
Kataoka et al.

(10) Patent No.: US 7,691,369 B2
(45) Date of Patent: Apr. 6, 2010

(54) CULTURED CELL CONSTRUCT WHICH CONTAINS SPHEROIDS OF CULTURED ANIMAL CELLS AND THE USE THEREOF

(75) Inventors: Kazunori Kataoka, Tokyo (JP); Hidenori Otsuka, Tsukuba (JP); Teruo Okano, Ichikawa (JP); Yukio Nagasaki, Moriya (JP); Yasuhiro Horiike, Nishitokyo (JP)

(73) Assignee: Transparent Inc., Chiba (JP)

( * ) Notice: Subject to any disclaimer, the term of this patent is extended or adjusted under 35 U.S.C. 154(b) by 17 days.

(21) Appl. No.: 12/230,916

(22) Filed: Sep. 8, 2008

(65) Prior Publication Data

US 2009/0011504 A1 Jan. 8, 2009

Related U.S. Application Data

(62) Division of application No. 10/484,839, filed as application No. PCT/JP02/07539 on Jul. 25, 2002, now Pat. No. 7,470,424.

(30) Foreign Application Priority Data

Jul. 26, 2001 (JP) .............................. 2001-226293

(51) Int. Cl.
C12N 5/02 (2006.01)
C12N 5/04 (2006.01)

(52) U.S. Cl. ...................... 424/93.1; 435/325; 435/347; 435/373

(58) Field of Classification Search ................ 424/93.1; 435/325, 347, 373
See application file for complete search history.

(56) References Cited

U.S. PATENT DOCUMENTS 5,976,826 A 11/1999 Singhvi et al.
6,132,979 A 10/2000 Murakami

OTHER PUBLICATIONS

International Search Report issued Nov. 5, 2002 in the International (PCT) Application PCT/JP2002/07539.
H. Otsuka et al., "Lactose Tanmatsu PEG Brush Hyomen no Bisai Kako ni Motozuka Kan-Spheroid no Kisokuteki Hairetsu Kozo (Kan-Spheroid Array) no Kochiki", Polymer Preprints, Japan, vol. 50, Aug. 28, 2001, No. 12, pp. 2810-2811.
H. Otsuka et al., "Cell-Based Biosensor (CBB) o Mezashita Kan-Spheroid no Kisokuteki Hairetsu Kozo (Kan-Spheroid Microarray) no Kochiki", The Japan Society of Mechanical Engineers, Dai 14 Kai Bioengineering Koenkai Koen Yoshishu, Mar. 1, 2002, pp. 23-24.
T. Takezawa et al., "Morphological and Immuno-Cytochemical Characterization of a Hetero-Spheroid Composed of Fibroblasts and Hepatocytes", J. Cell Sci., vol. 101, 1992, pp. 495-501.
Y. Sasaki et al., "Quantitive Comparison of Rat Hepatocyte Functions in Two Improved Culture Systems with or without Rat Liver Epithelial Cell Line", Cytotechnology, vol. 21, 1996, pp. 243-252.
T. Takezawa et al., "Ondo Kanjusei Sanjigen Baiyo Kishitsu to sono oyo", The Tissue Culture, vol. 19, No. 9, 1993, pp. 328-331.
Van Kooten et al., "Influence of substratum wettability on the strength of adhesion of human fibroblasts," Biomaterials, vol. 13, No. 13, 1992, pp. 897-904.
Takezawa et al., "Morphological and immuno-cytochemical characterization of a hetero-spheroid composed of fibroblasts and hepatocytes," Journal of Cell Science, vol. 101, 1992, pp. 495-501.

*Primary Examiner*—Ruth A Davis
(74) *Attorney, Agent, or Firm*—Wenderoth, Lind & Ponack, L.L.P.

(57) ABSTRACT

Parenchymal cells are cultivated on cultivated endothelial cells or cultivated fibroblasts which have been separated by a surface of a specific hydrophilic polymer, and which have been patterned. A culture which contains thus formed patterned spheroids of cultivated parenchymal cells is thereby provided by this invention. This culture maintains a function which is specific to the parenchymal cells over a long period of time.

4 Claims, 3 Drawing Sheets

CULTURED CELL CONSTRUCT WHICH CONTAINS SPHEROIDS OF CULTURED ANIMAL CELLS AND THE USE THEREOF

This application is a divisional of Ser. No. 10/484,839, filed Jan. 26, 2004, now U.S. Pat. No. 7,470,424 which is a 371 U.S. national stage of International Application No. PCT/JP2002/07539 filed Jul. 25, 2002.

TECHNICAL FIELD

This invention relates to a cultured animal cells and a construct of said cultured cells, and, more specifically, to a co-culture which contains spheroids of cultured cells and bio-devices which support said co-culture on their surface. Bio-devices and a co-culture per se are usable in the field of the physiological or pathophysiological examination of animal cells, transplantation, organo-regeneration engineering, hybrid-type prosthesis, etc.

BACKGROUND ART

From a functional viewpoint, animal cells are roughly classified into parenchymal cells and non-parenchymal cells. Among these, parenchymal cells fulfill functions of tissues or organs. For instance, hepatocytes, i.e., parenchymal cells of liver, undertake the synthesis, decomposition and storage of various substances, and are therefore very important basic units for a living organism.

Thus, there have been proposed some kinds of system for the cultivation of hepatocytes by which to imitate in vitro the expression of the function of hepatocytes in a living organism. For example, R. Singhvi et al., U.S. Pat. No. 5,976,826, disclose a process to cultivate hepatocytes in a cytophilic regions which are separated by regions that are composed of hydrophilic and cytophobic substances, and a device therefor. In this device, individual cells are seeded on surface regions (generally 1-2,500 $\mu m^2$, preferably 1-500 $\mu m^2$) which are composed either of compounds which have hydrophobic surface or charged moieties ($-COO^-$, $-PO_3H^-$) or of extracellular matrix proteins or the like. The cultivation which is mainly mentioned or intended in this U.S. Pat. No. 5,976,826 is regarded as so-called monolayer cultivation. On the other hand, there has also been tried three-dimensional architecture (three-dimensional growth pattern) with a view to improving the function of liver, e.g., enhancing the secretion of liver-enriched protein (M. Smalley et al. In Vitro Cell. Dev. Biol. Anim. (1999) 35, pp 22-32). In such three-dimensional culture methods, cell strains which have been derived from normal human liver are cultured on a gel of collagen type-I or of a special extracellular matrix.

There have further been provided devices by which to use cultured parenchymal or non-parenchymal cells conveniently in accordance with objectives such as toxicity test, and in which cultured cells are arrayed according to a certain pattern [e.g., Japanese Patent Application Laid-Open (Kokai) No. Hei 3 (1991)-7576 (a device for the control of cell-arrangement which device has cell-adhesive surface and non cell-adhesive surface), the above-mentioned U.S. Pat. No. 5,976,826 (the cultivation of hepatocytes), Japanese Patent No. 2973976 (the cultivation of endothelial cells), Japanese Patent Application Laid-Open (Kokai) No. Hei 7 (1995)-308186 (the cultivation of endothelial cells), etc.].

As mentioned above, it seems generally that the function of cultured cells which are given by three-dimensional architecture (three-dimensional growth pattern) is closer to that of hepatocytes in vivo than the function of cultured cells which are given by monolayer cultivation. Cultured cells of such a three-dimensional architecture system are liable to be peeled off the culture support, and, therefore, no three-dimensional structures have ever been realized on a patterned surface. Thus, three-dimensional architecture (three-dimensional growth pattern) is still unsatisfactory in the degree of expression of function and in the span of maintenance of function.

To begin with, organs of animals are constituted by tissues (groups of cells having similar function) of different properties. In most cases, cells which are units to constitute tissues keep their function through interaction between the same or different species of cells. Hence, from a viewpoint that heterotypic cellular interaction between parenchymal cells and adjacent non-parenchymal cells modifies cellular growth, migration and/or differentiation, S. N. Bhatia et al. set forth results of the study of the preservation of phenotype of hepatocyte which is given by the cocultivation of hepatocytes and fibroblasts which are non-parenchymal cells [S. N. Bhatia et al., The FASEB Journal, Vol. 13 (1999); 1883-1900]. In the monolayer of thus co-cultured hepatocytes which is enclosed by thus cultured non-parenchymal cells on the same plane, the intra-cellular albumin production ability, for instance, of hepatocytes which are located at a distance of three or four cells from the boundary between the monolayer of hepatocytes and the non-parenchymal cells decreases down to the same degree as that of purely cultured hepatocytes. In such a co-cultivation system, it is difficult for cells in an agglomerate of cultured hepatocytes to perform their liver-specific function stably.

Hence, the objective of the present invention is to provide a system of cultured animal cells by which to maintain specific function of parenchymal cells such as hepatocytes steadily and over a long period of time, and by which to keep micropattern stably when cells of the system are micropatterned.

DISCLOSURE OF INVENTION

Inventors of this invention have studied both a cultivation system of hepatocytes as one of two different species of cells, and the function of cultured hepatocytes which are obtained from said cultivation system. They have resultantly found out that, when hepatocytes are cultivated on a cellular monolayer of a certain region of cultivated endothelial cells or fibroblasts, not co-cultivated with non-parenchymal cells on the same plane so that interaction may occur via heterotypic interface as taught by the above-mentioned S. N. Bhatia et al., thus cultivated hepatocytes form a spheroid which adheres to the surface of said monolayer, and that thus formed spheroid exercises a function which is specific to hepatocytes, e.g., a function to produce albumin stably over a long period of time. Furthermore, both a co-culture which comprises the above-mentioned spheroid and a monolayer of cells, other than hepatocytes, which forms a substratum in contact with said spheroid, and a cultured cell construct (hereinafter sometimes referred to as spheroid/cultured cell monolayer/support) which comprises said co-culture and support therefor show resistance (stability) to peeling of each of cultured cells from the support. It has also been found out that, when applied to parenchymal cells, other than hepatocytes, which are capable of forming spheroid, or to non-parenchymal cells, such a cultured cell construct as mentioned above provides a spheroid-containing cultured cell construct which keeps function of these cells.

Among cells which form a substratum (or base) for said spheroid, endothelial cells or fibroblasts have generally strong proliferous potential and/or motility, and tend to migrate to, and grow on, the periphery of island on support on which the endothelial cells or fibroblasts are seeded and cultivated. The inventors have, however, further found out that the enclosing of said island with a surface of a certain hydrophilic and cytophobic polymer can prevent not only cultures of said endothelial cells or fibroblasts or the like but also spheroid which is formed on such cultured cells from migrating or moving from said island, and that a co-culture having a special form can be thus kept stable on a support.

Thus, this invention provides a cultured cell construct which comprises one, two or more co-cultures of different animal cells on a support. Each of co-cultures in such a cultured cell construct comprises a spheroid which is derived from cultivated cells of one of different cell species, preferably parenchymal cells, and a substantially single layer of cultivated cells which are derived from the other of said different cell species, which layer constitutes a substratum in contact with said spheroid and is capable of making cells which form said spheroid survive and function.

As another embodiment, this invention provides a biodevice which comprises a surface composed of two or more of the above-mentioned co-cultures.

As a further embodiment, this invention provides a process to prepare a cultured cell construct which comprises one, two or more co-cultures of different animal cells on a support in which co-cultures spheroids that have been formed from cultured cells are supported on separated plural islands, which process is characterized in that, on the surface of a material on which a co-culture is to be adhered, there is formed a polymer layer based on a polyethylene glycol segment one of whose terminal is unbound or covalently bound to a compound selected from the group consisting of mono- or oligosaccharides and oligopeptides which constitute a binding domain of ligand for an animal cell surface receptors, that the above-mentioned polymer layer is subjected to plasma treatment via a mask pattern having plural circular holes which are separated from one another at an interval of at least about 100 μm and which have a diameter of about 50-100 μm, that polymer layer is thus removed from islands which correspond to the above-mentioned holes, that, if necessary, cytophilic substance is applied to said islands from which polymer layer has been removed, that endothelial cells or fibroblasts are cultivated on the islands to form a monolayer of cultivated cells, and that cells which are different from said cultivated cells are cultivated on said cultivated cells to form a spheroid of the cells.

This invention also provides a co-culture per se which has been peeled off the support of the above-mentioned cultured cell construct.

This invention as explained above achieves an effect which is similar to the one attained by the cultivation of hepatocytes and endothelial cells or fibroblasts. For instance, a spheroid of cultivated hepatocytes maintains, at least for three weeks, an ability to produce albumin at a high level.

BEST MODE FOR CARRYING OUT THE INVENTION

Figure 1:
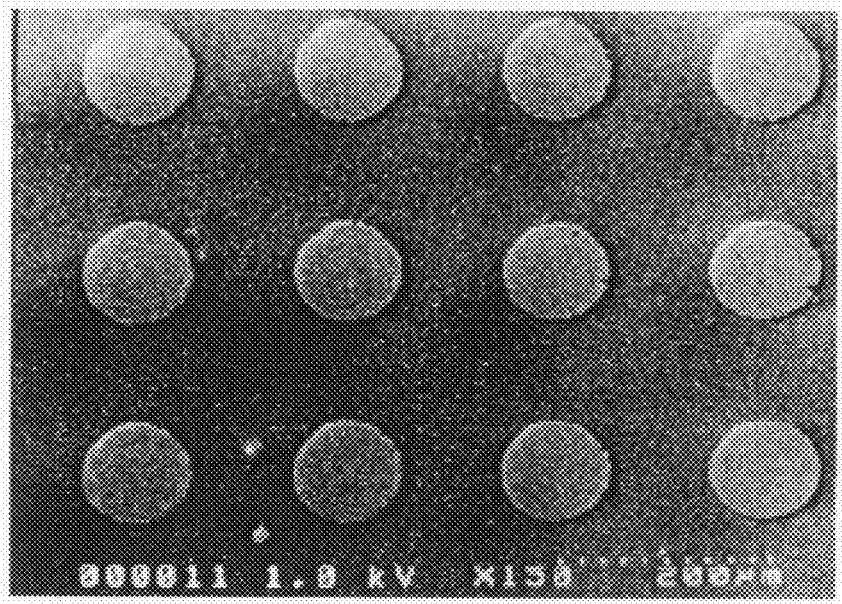
FIG. 1 is a micrograph in place of a drawing which shows exposed pores on glass surface that were formed in accordance with mask pattern as prepared in Example.

One of the different animal cells which are to be co-cultivated in accordance with this invention may be cells any of any species so long as they are capable of forming a spheroid through co-cultivation as mentioned later. Preferably, however, said cells are parenchymal cells. Parenchymal cell means a cell which fulfills functions of a tissue or organ. For instance, parenchymal cell of liver is hepatocyte, and parenchymal cell of lung is alveolar epithelial cell. Any cell that falls under this definition and suits the purpose of this invention is to be called parenchymal cell in this invention. Examples of parenchymal cells which are primarily intended to be used in this invention include, although not restrictive, hepatocytes, beta cells of pancreas, cardiac muscle cells, glia cells, skin epithelial cells (keratinocytes), chondrocytes, osteocytes and embryonal or adult stem cells. However, not only the above-defined parenchymal cells but also non-parenchymal cells are included in the above-mentioned animal cells so long as they are capable of forming a spheroid and suit the purpose of this invention, as stated above.

The other one of the different animal cells which are to be co-cultivated may be any species of cells so long as they, when co-cultivated, serve to help the above-mentioned spheroid-forming cells to survive and function, and so long as they are different from said spheroid-forming cells. Endothelial cells, epithelial cells and fibroblasts can be mentioned as examples of such cells. Preferable are endothelial cells, in particular angio endothelial cells, among which funicular vein endothelial cells are most desirable. Fibroblasts are also preferable. Fibroblasts are mesoblast-derived cells which are dispersed in almost all tissues of an animal body. Fibroblasts are to be chosen according to the cells which form a spheroid when cultivated as mentioned above, or, in other words, fibroblasts which play important roles for the morphogenesis of an organ where the spheroid-forming cells exist are preferably used. A combination of different animal cell species which are to be co-cultivated also includes, in addition to the above-mentioned ones, a combination of non-parenchymal cell-non-parenchymal cell such as fibroblast-endothelial cell and epithelial cell-endothelial cell, and a combination of parenchymal cell-parenchymal cell such as cardiac muscle cell-hepatocyte and beta cell of pancreas-hepatocyte, although not restrictive.

Animals from which the above-mentioned cells are originated may be of any kind, examples of which include poultry and mammals, in particular human being.

When these different animal cell species are co-cultivated in accordance with this invention, endothelial cells, epithelial cells or fibroblasts form substantially a monolayer of cultivated cells as anchorage dependent cells or feeder cells on the surface of culture support, and, subsequently, cells, preferably parenchymal cells, which have been cultivated on said monolayer and which are different from the cells that form the monolayer, come into contact with the cultivated cells which constitute said monolayer, and, through heterotypic interaction, maintain a function specific to corresponding cells stably for a long period of time. The phrase "form substantially a monolayer of cultivated cells" means that at least 80%, preferably at least 90%, more desirably at least 95%, of region on which to form said cellular layer is composed of monolayer of cultivated cells. As for co-cultivation, if only the above-mentioned different animal cells are cultivated together for some period, it comes under the definition of "co-cultivation". In an instance to facilitate the understanding of this invention, endothelial cells or fibroblasts for example are firstly cultivated to form a monolayer, and, subsequently, these feeder cells and parenchymal cells are cultivated together.

The above-mentioned endothelial cells, epithelial cells or fibroblasts are cultivated on an island on the surface of culture support, and, on this island, there is constructed a feeder layer which is composed of thus cultivated cells, and, later, there is formed a construct of cultivated cells which comprises a co-culture that is composed of said feeder layer and a spheroid which is in direct contact with said feeder layer and which is preferably originated from parenchymal cells. A spheroid which is formed from a culture of some species of cells means, as is known from the term "spheroid", a substantially spheric agglomerate of cultivated parenchymal cells, which has a shape as shown by the confocal laser micrograph that is attached hereto as FIG. 5, or a shape which resembles the same. The phrase "substantially spheric" is intended to include not only a completely spheric shape but also a slightly flat one.

The above-mentioned island is subject to no restrictions so long as it achieves the purpose of this invention. Generally, however, the island may have any shape including circle, polygon such as quadrilateral, ellipse, etc., that has an area of about 1,000 to about 200,000 μm$^2$, preferably about 1,500 to about 50,000 μm$^2$. Circular shape is preferable, in which case the circle has a diameter of about 40 to about 500 μm, preferably about 50 to 200 μm, more desirably about 50 to about 100 μm. In a construct of cultured cells wherein an island with a larger diameter supports a feeder layer and further a spheroid thereon, each culture or co-culture may possibly show a tendency to peel off the surface of support, or the spheroid may possibly fail to stably maintain the function of parenchymal cells from which the spheroid has been originated.

As stated above, when endothelial cells, epithelial cells or fibroblasts are cultivated on such an island as mentioned above, thus cultivated cells may, under circumstances, migrate out of the island, making it impossible to form a culture on the island as specified above.

In order to evade such inconveniences, this invention provides a surface, produced by hydrophilic and cytophobic substance, which encircles said island. Details of such a substance are mentioned later. Attention is drawn to the fact, for the present, that, although the above-mentioned U.S. Pat. No. 5,976,826 teaches that sialic acid, lectin, polygalactose and other carbohydrates mediate cell binding, and although P. H. Weigel et al., J. Bio. Chem. Vol. 254 (1979) 10830-10838 exemplifies the fact that hepatocytes are specifically adhered to saccharide which has covalently bound to flat polyacrylamide gel, what is called "cytophobic substance" in this invention is sometimes independent of, or even opposite to, these teachings.

Concretely, hydrophilic and cytophobic substance in accordance with this invention has properties as follows: the above-mentioned anchorage-dependent cultivated cells or feeder layer-forming cultivated cells cannot adhere to a surface which is made of said hydrophilic and cytophobic substance under cultivation conditions as mentioned later, or, even though adhered, said anchorage-dependent cultivated cells or feeder layer-forming cultivated cells can be easily detached by mild cleansing or rinsing, and, thus, when parenchymal cells are to be cultivated later, said anchorage-dependent cultivated cells or feeder layer-forming cultivated cells cannot be cultivated stably for a long period of time, or, furthermore, also the cultivated parenchymal cells are hard to adhere to this surface made of the hydrophilic and cytophobic substance of this invention. A part of substance which is capable of forming such a surface as mentioned above may be a substance which forms a cytophobic or biophobic monomolecular layer as set forth in the above-mentioned U.S. Pat. No. 5,976,826. Preferable examples include compounds which contain a portion of polyethylene glycol (hereinafter may sometimes be referred to as "PEG"). In said U.S. patent, for instance, there is concretely used a compound [e.g., $HS(CH_2)_{11}(OCH_2CH_2)_6OH$] which has six ethylene glycol units.

Furthermore, what is preferably used as cytophobic substance in this invention and gives a much more unique feature to this invention is saccharide derivative or peptide derivative each of which is based on a polyethylene glycol segment to one of whose terminals is covalently bound a mono- or oligosaccharide or a certain kind of oligopeptide each of which constitutes a binding domain of ligand to cell surface receptors, or polysaccharide, although it is said that hepatocytes adhere to saccharides.

Hence, a surface which encircles the above-mentioned island is preferably made of polymer based on PEG segment although such a surface can also be made of such compounds as mentioned in the U.S. Pat. No. 5,976,826. The phrase "based on PEG segment" means that said polymer, when it has no sugar residue, comprises PEG segment so that thus formed surface is covered mainly with free chain of PEG segment. So long as such an action is exerted, said polymer may be homopolymer, block copolymer or a derivative thereof. Incidentally, "free chain" means a state of polymer chain in which said segment can take a substantially free conformation when placed in an aqueous medium.

Although not restrictive, such a polymer, or sugar derivative which has a sugar residue, or peptide derivative which has an oligopeptide residue has the following general formula (I):

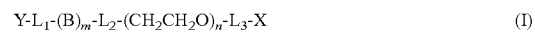

In the above-mentioned formula, $L_1$, $L_2$ and $L_3$ independently denote valence bond, oxygen atom or linker with the proviso that, when m is 0 (zero), $L_1$ and $L_2$, taken together, may denote valence bond, oxygen atom or linker.

B denotes a compound of the following formula:

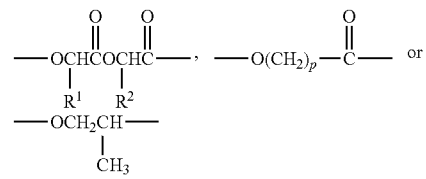

wherein $R^1$ and $R^2$ independently denote a hydrogen atom or an alkyl group having one to five carbon atoms; p denotes an integer of 2 to 5; X denotes a hydrogen atom, a sugar residue or a peptide residue; Y denotes a hydrogen atom or a functional group which is capable of binding or adhering said polymer to the surface of device; m denotes an integer of 0-10,000; and n denotes an integer of 10-20,000.

As for $L_1$, $L_2$ and $L_3$, $L_1$ denotes a valence bond or a linker of $—(CH_2)_q—O—$, $—(CH_2)_q—COO—$, $—(CH_2)_q—S—$ or —CO—$(CH_2)_q$—NH—. When m denotes 0 (zero), $L_1$ and $L_2$, taken together, denote a linker as defined above with respect to $L_1$. Incidentally, the mark q denotes an integer of 2 to 6. When m is other than 0 (zero), $L_2$ denotes —O— or —O—$CH_2CH_2$—O. $L_3$ denotes a valence bond or —$(CH_2)_r$— wherein r may denote an integer of 1 to 6.

As the above-mentioned polymer, there may be used the polymers as are shown in WO 96/32434 (or U.S. Pat. No. 5,037,969) which was disclosed by a part of inventors of the present invention, WO 96/33233 (or U.S. Pat. No. 5,925,720) and WO 97/06202 (or U.S. Pat. No. 5,929,177) and in Jo et al., Biomaterials, 21, 605-612, 2002, or a slight modification of these polymers, or polymers which are to be produced in a way similar to these patents or document.

In this invention, a polymer of the above-mentioned general formula (I) wherein X denotes a sugar residue, e.g., monosaccharides or oligosaccharides (which may have up to 11 sugar units, preferably up to seven), in particular disaccharides, which constitute a binding domain of ligand to cell surface receptors, is preferably used since a surface which is formed from such a polymer effectively prevents the adhesion of what is called cultivated cells in this invention. A polymer wherein X denotes monosaccharides is disclosed in the above-mentioned WO 96/32434 (or U.S. Pat. No. 5,037,969). In accordance with the method as mentioned in this WO 96/32434, any sugar residue as desired can be made to be supported. A slight modification of said method gives a polymer wherein X denotes polysaccharide residue or oligosaccharide residue. A polymer wherein X denotes sugar residue can also be obtained by another method as disclosed in the above-mentioned WO 96/33233 (or U.S. Pat. No. 5,925,720), according to which acetal group of a polymer having an acetal group at X is converted into aldehyde group, which in turn is subjected to a reductive amination reaction with an amino group which has previously been introduced into mono- or oligosaccharide. As said mono- or oligosaccharides, those which contain at least one galactopyranosyl are preferably used. Although non-restrictive, examples of such oligosaccharides include lactose and various kinds of sialooligosaccharide. Hydrophilic polymer of the above-mentioned general formula (I) wherein X denotes an oligopeptide residue which constitutes a binding domain of ligand to cell surface receptors is also preferably used in this invention. Said ligand may be lectin water-soluble signal molecule (e.g., protein hormone, growth factor protein). As examples of such an oligopeptide, there may be mentioned, although non-restrictive, one which is composed of up to 10 amino acid residues including at least arginine (Arg), glycine (Gly) and aspartic acid (Asp), and which can be water-soluble as a whole.

In addition to the above-mentioned sugar derivatives of polymer based on PEG to which sugar has been covalently bound, polysaccharide per se such as polygalactose, sialic acid and others to which lectin can bind may be used as a hydrophilic polymer in this invention. Anyone skilled in the art would see what hydrophilic polymer is like, from the above-recited polymers. Under cell-cultivation conditions of this invention, hydrophilic polymer means either a polymer the whole of which is water-soluble under an ambient condition, or a polymer wherein polymer (polyethylene in the above-mentioned example) which corresponds to polymer-constituting segment is water-soluble. Those skilled in the art would be able to easily choose concrete polymer which is conveniently usable in this invention, from the above-mentioned polymers in the light of Examples which are mentioned later.

Y, or Y-$L_1$-(B)— under circumstances, in general formula (I) may be chosen suitably according to the properties of substratum (base plate, film, coating film or deposited film which forms directly or indirectly a surface of culture support or a surface of device) on which a surface of said hydrophilic substance is to be formed. For instance, said surface of culture support may have a surface to which a polymer of general formula (I) can surely be adhered or bound. Although non-restrictive, when said surface of culture support is coated with silicone, or when a surface which has hydroxyl group has been rendered hydrophobic by silane treatment, Y-$L_1$-(B)— may be so selected as to form a block copolymer wherein m denotes an integer other than 0 (zero), e.g., five or more, in the general formula (I), and, thus, with use of the hydrophobicity of thus obtained ester segment, said polymer may be adhered to said surface of culture support to make a surface of hydrophilic substance. In such an instance, when, with a view to enhancing the adhesion of polymer, a homopolymer which corresponds to said ester segment is previously adhered to the surface of support and then said block copolymer is adhered, there is obtained a surface of hydrophilic substance which shows good resistance to peeling etc.

When a surface of support has such a functional group as recited in the above-mentioned U.S. Pat. No. 5,976,826, the group Y may be another functional group which reacts with the above-mentioned functional group to form a covalent bond such as —CONH—, —CONHCO—, —S—S—, —O—, —Si—O—, —NH—, etc. How to introduce such a functional group to Y, and examples of polymer having such a functional group are given in the above-mentioned U.S. patent which was applied for by a part of the present inventors. How to provide a surface of support which has a functional group is partially given in the above-mentioned U.S. Pat. No. 5,976,826. Such a surface of support can also be prepared by subjecting a surface which has been coated with polyamide, polyurethane, polyacrylamide, etc., to plasma treatment by any known method, or by subjecting a monomer which has a protected functional group corresponding to the above-mentioned functional groups to any known plasma treatment and, if necessary, eliminating the protective group.

When, on the other hand, the surface of support is made of metal such as gold, silver and copper, the group Y is desirably a mercapto group, by which a polymer of the general formula (I) can be adhered to substratum through so-called chemical adsorption, and, thus, a desired surface can be produced.

If necessary, the above-mentioned island may be treated so that its surface may be cytophilic. The term "cytophilic" in this specification means that, when the afore-mentioned endothelial cells, epithelial cells or fibroblasts are cultivated on a surface having such a property, thus cultivated cells adhere, and thus adhered cells are not detached by mild cleansing or rinsing. Such a surface may be formed of a compound which has hydrophobic group (e.g., hydrocarbon group, alkyl silyl group, alkyl fluoride group, etc.) or a compound (including protein which constitutes extracellular matrix) which has charged group (e.g., —$COO^-$, —$PO_3H^-$, etc.). Such a surface can be prepared by replacing hydrophilic substance (or hydrophilic polymer) with one of the above-recited compounds in the above-mentioned process to produce a surface of hydrophilic substance.

Islands having a cytophilic surface can be produced by any method well known to those skilled in the art, such as a pattern-forming method and a micropatterning method. Preferably, however, islands having a cytophilic surface are produced in the following manner: a surface of hydrophilic polymer is formed on a suitable support, and, on this surface, there is placed a pattern on which holes corresponding to islands are arrayed in a desired manner, and, via these holes, a plasma treatment with use of $H_2+N_2$ is conducted to remove polymer layer which has formed said surface, and, then, thus obtained islands are, if necessary, treated with a compound which may form the above-mentioned cytophilic surface. The above-mentioned term "if necessary" is intended to mean that, if a surface (which may be a surface of device per se) on which a surface of hydrophilic polymer has been placed is a cytophilic surface which yields to no adverse effect from the above-mentioned plasma treatment, the above-mentioned optional treatment is needless.

Interval of thus produced islands is preferably about 100 µm at least. When plural islands are separated, at this interval, by surface domain of hydrophilic polymer in a cultivation system wherein endothelial cells or fibroblasts are selected as anchorage dependent cells or feeder layer-forming cells, there occurs substantially no connection or crosslinkage among thus cultivated endothelial cells or fibroblasts and cultivated parenchymal cells, in particular among hepatocyte spheroids, on the above-mentioned islands. The passage "there occurs substantially no connection or crosslinkage" means that the morphological connection of spheroids of cultivated hepatocyte with one another on a large number of islands accounts for less than 10%, preferably less than 5%, more desirably 0%.

Such a construct of cultivated cells which supports a culture that contains spheroid formed from cultivated cells and arrayed (or patterned) in a desired manner can also be obtained conveniently by a process for the preparation of a construct of cultivated cells as another embodiment of this invention.

(A) The surface of a support on which cells are to be cultivated is coated, by spin coating, with a solution, in an organic solvent (such as toluene) or water, of a polymer based on PEG segment, preferably a polymer of the above-mentioned general formula (I), especially desirably a polymer of said formula wherein X denotes a sugar residue or an oligopeptide residue. When the surface of said support is made of glass, if hydroxyl group on said surface is previously rendered hydrophobic by a treatment with a hydrophobic silane coupling agent, subsequent treatment to render islands cytophilic may sometimes become needless. Silane treatment may be conducted by any known method, e.g., the one which is mentioned in H. Otsuka et al., Biomacromolecules, 2000, 21-27. Incidentally, a sugar residue may be introduced into the above-mentioned polymer by the following method: a polymer of the general formula (I) wherein X denotes acetal is previously applied by spin coating; later, amino group of a sugar into which the amino group has previously been introduced is subjected to a reductive amination reaction with aldehyde which has been exposed by the deblocking of the above-mentioned acetal. It is hard to specify the thickness of the resultant polymer layer since optimum thickness varies depending on the species of polymer used. Anyway, a polymer layer is required to have a thickness which prevents adhesion between feeder forming cells or cells different therefrom, e.g., cultivated parenchymal cells, on an island and corresponding cells on another island. Any skilled person would be able to determine such a thickness by a simple experiment. Although non-restrictive, a thickness of a general monomolecular film would be a minimum.

(B) On the surface which has been obtained in step (A), a mask pattern which has plural holes of islands (preferably circular ones having a diameter of about 50-500 µm) is placed, and a plasma treatment is conducted with use of $H_2+N_2$ by a plasma generator, and, thus, polymer layer of domains corresponding to the holes are destructed and removed, and, for instance, hydrophobic-treated surface is exposed.

(C) If necessary, the surface which has been exposed by the removal of polymer layer may be either subjected to plasma polymerization with a monomer having a cytophilic group via the above-mentioned mask pattern, or coated with a polymer derived from said monomer, thus to be modified cytophilic.

(D) On thus obtained surface having cytophilic islands, there are cultivated, for instance, endothelial cells (if suitable, cell on the market, for example, "human funicular vein endothelial cell" provided by Dainippon Pharmaceutical Co., Ltd.) with use of a culture medium by which such cells can be cultivated (if suitable, culture medium on the market, for example, "VE medium" provided by Dainippon Pharmaceutical Co., Ltd.), and, thus, a layer of cultivated cells is formed. This cultivation can be conducted by a method as disclosed in Japanese Patent 2973976 or a modification thereof.

(E) On the feeder layer of cultivated cells as formed in the step (D), cells which are different from the cells that form said layer of the cells, preferably parenchymal cells, are cultivated. Although primary cells are preferable for the above-mentioned cells such as parenchymal cells, any species of cells of cell line (or strain) or any transformed or transfected cells will do so long as they are capable of forming a spheroid of cultivated cells on the above-mentioned layer of cells when cultivated according to the method of this invention. Both endothelial cells or fibroblasts which form a feeder layer and cells which form spheroid, preferably parenchymal cells, are usable regardless of their origin. It is preferable, however, to use animal cells of the same origin. These cells may be cultivated by any known cultivation method (see, for instance, S. N. Bhatia et al., Biotech. Prog. 1998, 14, 378-387). When hepatocytes are used as the above-mentioned cells, spheroids of cultivated hepatocytes are usually formed after at least 24 hours on a feeder layer of cultivated cells on the above-mentioned islands.

Other cells than hepatocytes are capable of forming spheroids of cultivated parenchymal cells on a feeder layer of cultivated cells on the above-mentioned islands when cultivated by any known cultivation method. With regard to the cultivation of cardiac muscle cells, see T. Shimizu et al., Journal of Biomedical Materials Research, 60(1) (2002): 110-117 and G. Illiano et al, American Journal of Hypertension 15 (2002): 638-643; with respect to the cultivation of glia cells, see C. Gamboa et al, Neurochemistry International 40 (2002): 397-403; and with respect to the cultivation of beta cells of pancreas, see J. L. Petit-Thevenin et al., Biochemica et Biophysica Acta 1530 (2001): 184-198, these references being non-restrictive.

Animal cells which are to be used in this invention are preferably primary cells as obtained by any known method such as surgical ones. Also usable are those which are available on the market from suppliers such as the Human Science Promotion Foundation.

Thus obtained co-culture is usable either for bio-devices whose surface is made of a cultivated cell construct per se which has the co-culture on the surface of a support, or for bio-devices whose surface is formed from said co-culture. Although not restrictive, examples of such bio-device include a device for the test of toxicity of cultivated parenchymal cells, a device for the screening of substances which activate the function of cultivated parenchymal cells, a device for medical support of the deficiency of parenchymal cells and a device for trial examination of the physiological activity of parenchymal cells.

A co-culture (comprising a spheroid formed from cultivated cell and a substantially single layer of cultivated cell which forms a substratum in contact with said spheroid and which is different from the cell that forms said spheroid) in accordance with this invention which is supported on bio-devices is retained on the surface of said device stably over a long period of time, and also maintains function (such as insulin-secreting function in the case of beta cell of pancreas, pulsation function in the case of cardiac muscle cell, with regard to cells other than hepatocytes) which is specific to each parenchymal cells. In a bio-device which is produced from hepatocytes for instance, morphologically uniform spheroids are supported on a predetermined arrayal pattern. The shape of spheroid on one island is substantially independent from that of spheroid on another. Furthermore, spheroid on a bio-device in accordance with this invention maintains a high-level hepatocyte function (e.g., high-level albumin-production ability) for at least three weeks stably. Such a bio-device is, therefore, usable for the screening of environment or substance which may have an influence on hepatic function. Such an influence can be evaluated by the monitoring of the morphological change or product of spheroid, e.g., change in albumin-production ability.

Co-culture which is contained in the afore-mentioned culture cell construct can be peeled off the support by a physical or biochemical treatment. Thus peeled culture per se is an embodiment of this invention, and is usable in transplantation, organo-regeneration engineering and hybrid-type prosthesis.

This invention is further explained by concrete examples as follows. The examples are provided only with a view to facilitating the understanding of this invention.

a) Preparation of Cell Culture Bed:

A white slide glass (26×76×0.8 mm/Takahashi Giken Glass Co., Ltd.) was boiled with sulfuric acid/hydrogen peroxide (50/50) for 60 minutes, and was then washed. Subsequently, the surface of this glass was rendered hydrophobic by a silane coupling treatment with a 2% [3-(methacryloyloxy) propyl]trimethoxysilane solution in ethanol/water (95/5). The surface of thus prepared hydrophobic-treated slide glass was coated with a 4% solution, in toluene, of polylactide having a molecular weight of 20,000 by spin coating, and subsequently with a 2% solution, in toluene, of lactose-PEG/PLA which had been obtained by reductive amination of aldehyde, converted from acetal-polyethylene glycol (molecular weight: 6,000) copolylactide (molecular weight: 8,000; hereinafter referred to as acetal-PEG/PLA), with aminophenyl lactose by spin coating, and, thus, a polymeric layer surface with a thickness of about 100 µm was formed. On thus formed polymeric layer surface, there was placed a mask pattern having circular pores of 100 µm which were separated at an interval of 100 µm, and, then, a plasma treatment of $H_2+N_2$ was conducted [ICP power: 500 W. Bias power: 30 W (Vdc=60 V), $N_2+H_2$=50 sccm/30 sccm, $2\times10^{-5}$ Torr]. As a result of this plasma treatment, there were formed pores in which glass surfaces were exposed, according to the above-mentioned mask pattern (see FIG. 1).

Figure 2:
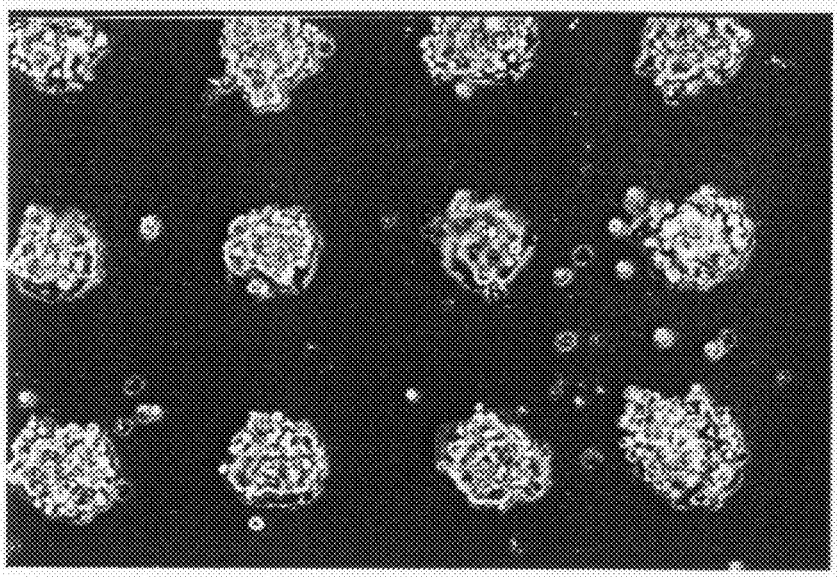
FIG. 2 is a micrograph in place of a drawing which shows cultivated endothelial cells adhered to cell culture bed as derived from patterned pores of FIG. 1.
Figure 3:
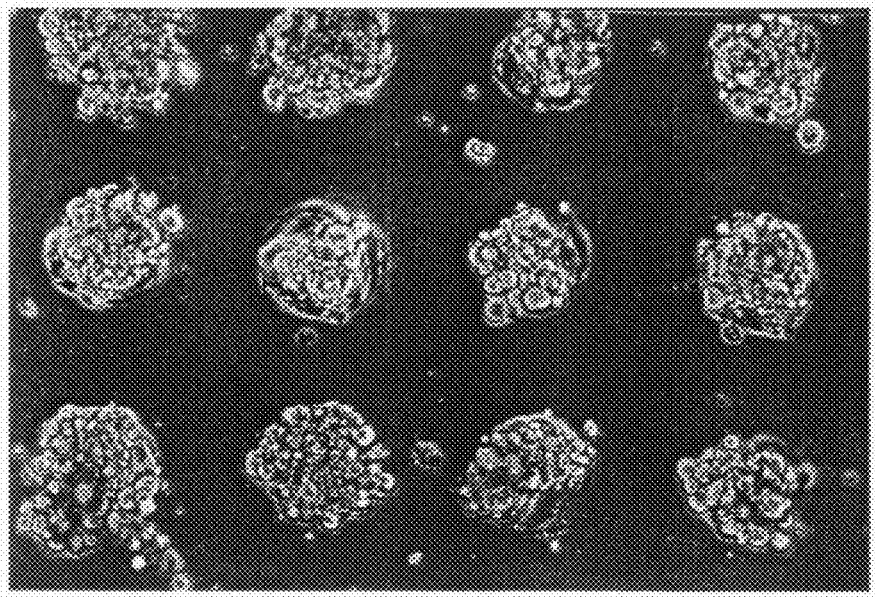
FIG. 3 is a micrograph in place of a drawing which shows spheroids formed of hepatocytes that have adhered only on endothelial cells which have formed domains according to a pattern as shown in FIG. 2.
Figure 5:
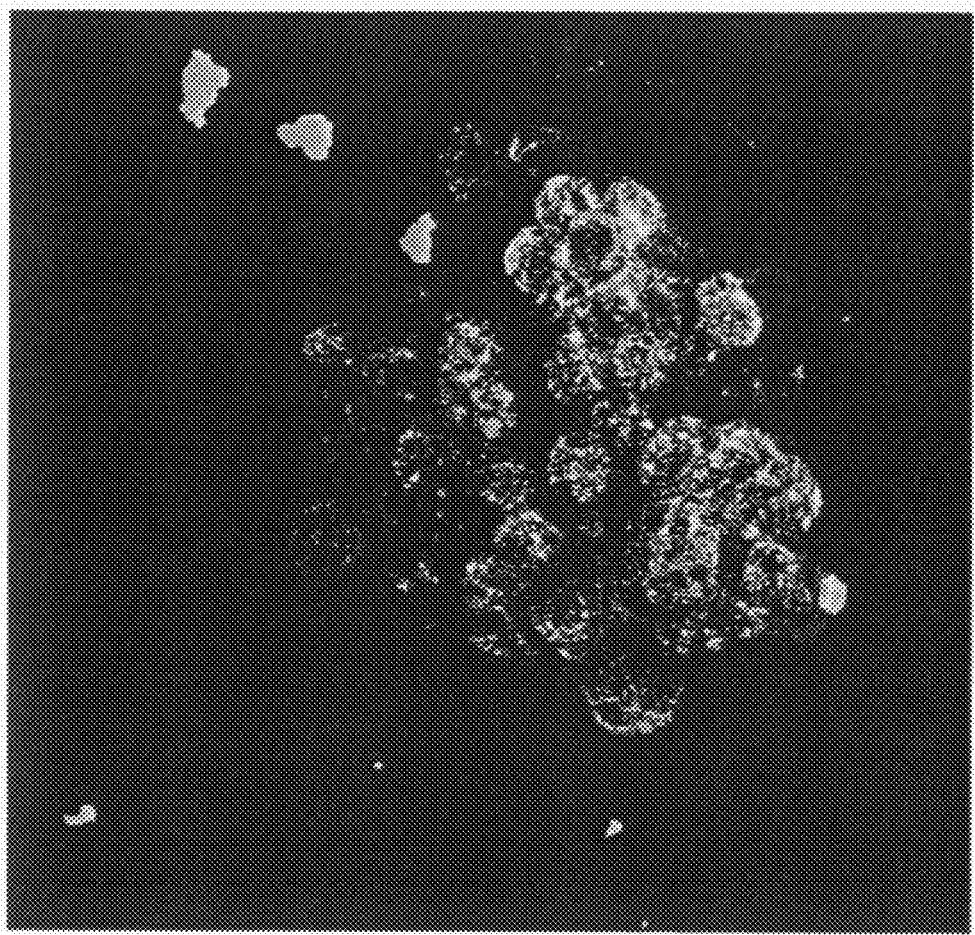
FIG. 5 is a confocal laser micrograph in place of a drawing which shows a three-dimensional image of hepatocyte spheroid that has been formed on endothelial cells arrayed according to a pattern.

On the above-mentioned surface, there was applied Dulbecco's modified Eagle's medium (DMEN, Gibco) (supplemented with insulin, fetal bovine serum, glucagon, epidermal growth factor, penicillin, hydrocortisone and streptomycin), and, thus, there was formed cell adhesion domain (or cell culture bed) corresponding to the above-mentioned pores.

b) Cell Cultivation:

On the cell culture bed as obtained in the above a), angioendothelial cells (Bovine aortic endothelial cells) were seeded at a cell density of $1\times10^6$ cells/cm$^2$, and were then statically cultured in an atmosphere of 5% $CO_2$ at 37° C. for 24 hours. Thus, endothelial cells were adhered according to the glass pattern of exposed pores (see FIG. 2). Subsequently, primary culture of hepatocytes which had been prepared from rat's liver by collagenase perfusion was seeded at a cell density of $1\times10^6$ cells/cm$^2$, and was then statically cultured in an atmosphere of 5% $CO_2$ at 37° C. for 24 hours. Resultantly, hepatocytes were adhered only to the endothelial cells which had formed domains according to the above-mentioned pattern, and, thus, an array of spheroids was formed (see FIG. 3). These hepatic spheroids maintained hepatic function (e.g., albumin-producing ability) at least for three weeks, and, thus, cytoskeleton was observed (FIG. 5 shows a three-dimensional enlarged image of spheroid).

Figure 4:
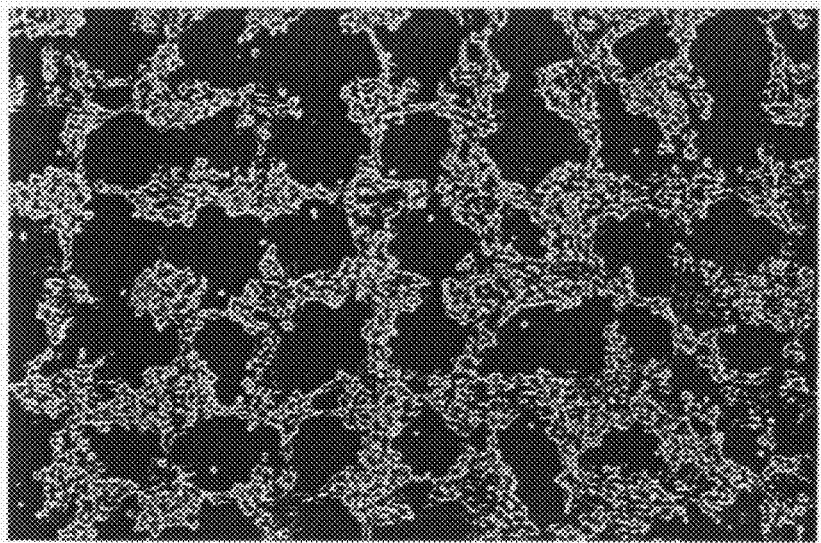
FIG. 4 is a micrograph in place of a drawing which shows that, when interval between circular holes of a size of 100 μm is less than 100 μm, cultivated endothelial cells may make a connected pattern.

Also on the surface of lactose-PEG/PLA, when the interval between circular holes of a size of 100 µm was less than 100 µm, adjoining endothelial cells got connected to each other, and, when the interval was much shorter, cells formed a sheet under circumstances (see FIG. 4). Generally, when there is no patterned layer of endothelial cell, there is formed no spheroid pattern of cultivated hepatocytes.

INDUSTRIAL APPLICABILITY

In thus obtained array of hepatic spheroids, hepatic function is maintained over a long period of time. Furthermore, one culture dish may contain tens of thousands (theoretically an infinite number) of hepatic spheroids, and, therefore, such a culture dish is usable for the medicinal assay of tens of thousands of medicines at a time. Besides, co-culture, e.g., cultivated hepatic spheroid, which is to be peeled off said array may be used in the field of transplantation or liver-regeneration engineering. Thus, this invention is usable in an industry which is involved with examination to evaluate medicinal action or in a medical support industry.

The invention claimed is:

1. A process for the preparation of a cultured cell construct which comprises at least two co-cultures of different animal cell species on a support wherein, in the co-cultures, spheroids are carried on a monolayer of cultivated cells on separated plural islands, which process comprises the following steps:

preparing a support which has plural islands thereon, said islands being separated from one another at an interval of at least about 100 µm, being substantially circular and having a diameter of about 100 µm to about 500 µm;

culturing endothelial cells or fibroblasts on said islands so as to form a feeder layer originated from said endothelial cells or fibroblasts; and culturing parenchymal cells on said monolayer so as to form a substantially spheric agglomerate of cultured parenchymal cells, the parenchymal cells being selected from the group consisting of hepatocytes, beta cells of pancreas, cardiac muscle cells, glia cells, skin epithelial cells (keratinocytes), chondrocytes, osteocytes and adult stem cells; wherein the surface of support is produced from a hydrophilic and cytophobic substance so that said islands may be separated from one another.

2. The process for the preparation of a cultured cell construct of claim 1 wherein the parenchymal cells are hepatocytes.

3. The process for the preparation of a cultured cell construct of claim 1 wherein the hydrophilic and cytophobic substance is a polyethylene glycol-based polymer.

4. The process for the preparation of a cultured cell construct of claim 1 wherein the islands are substantially circular and have a diameter of about 100 µm to about 200 µm.

* * * * *